(12) United States Patent
Holowecky et al.

(10) Patent No.: US 11,744,622 B2
(45) Date of Patent: Sep. 5, 2023

(54) SURGICAL SYSTEM AND METHOD INCLUDING CERCLAGE WITH LOOP

(71) Applicant: Arthrex, Inc., Naples, FL (US)

(72) Inventors: Allen Holowecky, Naples, FL (US); Andrew R. Curran, Meridian, ID (US)

(73) Assignee: Arthrex, Inc., Naples, FL (US)

( * ) Notice: Subject to any disclaimer, the term of this patent is extended or adjusted under 35 U.S.C. 154(b) by 51 days.

(21) Appl. No.: 17/335,175

(22) Filed: Jun. 1, 2021

(65) Prior Publication Data

US 2022/0378486 A1    Dec. 1, 2022

(51) Int. Cl.
    *A61B 17/82*     (2006.01)
    *A61B 17/06*     (2006.01)
    *A61B 17/56*     (2006.01)

(52) U.S. Cl.
CPC ........ *A61B 17/82* (2013.01); *A61B 17/06166* (2013.01); *A61B 2017/564* (2013.01); *A61B 2017/567* (2013.01)

(58) Field of Classification Search
CPC .......................... A61B 17/82; A61B 17/06166
See application file for complete search history.

(56) References Cited

U.S. PATENT DOCUMENTS

| | | | |
|---|---|---|---|
| 5,540,703 A | 7/1996 | Barker, Jr. et al. | |
| 8,162,997 B2 | 4/2012 | Struhl | |
| 8,876,900 B2 | 11/2014 | Guederian et al. | |
| 10,433,890 B2 | 10/2019 | Golden et al. | |
| 2011/0295284 A1 | 12/2011 | Purdue et al. | |
| 2018/0296318 A1 | 10/2018 | Wallace et al. | |
| 2018/0368895 A1 | 12/2018 | Cox | |
| 2019/0142486 A1 | 5/2019 | Miller | |
| 2019/0374268 A1 | 12/2019 | Golden et al. | |
| 2020/0315677 A1* | 10/2020 | Hachem | ................. A61B 17/82 |

OTHER PUBLICATIONS

Acromioclavicular joint repair using a suture cerclage tensioning system. Youn et al. (2019), retrieved from "https://www.arthroscopytechniques.org/article/S2212-6287(19)30181-1/fulltext."
Infinity-Lock™ Button System. Neoligaments. (n.d.). https://www.neoligaments.com/product/infinity-lock/.
LockDown™ ACJ Ligament. Atlantic Surgical. (n.d.). https://www.atlanticsurgical.ie/product/lockdown/.
Open acromioclavicular joint reconstruction with semitendinosus allograft utilizing the cerclage technique. Makhni et al. (2020).
Reconstruction of displaced acromio-clavicular joint dislocations using a triple suture-cerclage: description of a safe and efficient surgical technique. BioMed Central. Sandmann et al. (2012).
International Search Report and Written Opinion for PCT/US2022/027409 dated Aug. 12, 2022.

* cited by examiner

Primary Examiner — Sameh R Boles
(74) Attorney, Agent, or Firm — Carlson, Gaskey & Olds, P.C.

(57) ABSTRACT

This disclosure details a surgical system and method, which is useful for treating an acromioclavicular (AC) joint. In an example, the disclosed system includes a cerclage which is provided relative to a coracoid process and which includes a loop. In that example, a clavicle is held relative to the coracoid process using a clavicle fixation assembly, which includes suture passed through the loop of the cerclage.

5 Claims, 6 Drawing Sheets

SURGICAL SYSTEM AND METHOD INCLUDING CERCLAGE WITH LOOP

BACKGROUND

Cerclages are sometimes used to maintain the relative position of fractured bone fragments to promote healing. Known cerclages include materials such as cable (i.e., wire) or fabric, and are provided by wrapping the cable or fabric around a fractured bone. After wrapping, the cable or fabric is then locked into place relative to the bone, such as with a plug or clip.

SUMMARY

This disclosure details a surgical system and method including a cerclage with a loop. The system and method is useful in treating various displaced, dislocated, cut, and/or fractured bones. The system and method is useful in treating an acromioclavicular (AC) joint. In an example, the disclosed system includes a cerclage which is provided relative to a coracoid process and which includes a loop. In that example, a clavicle is held relative to the coracoid process using a clavicle fixation assembly, which includes suture passed through the loop of the cerclage.

The cerclage is a separate, dedicated assembly provided about a bone, such as the coracoid process, and is connectable to other assemblies, such as a clavicle fixation assembly, via the loop. As such, assemblies connected to the cerclage via the loop can be adjusted independent of the cerclage. Further, in an example, the cerclage can be installed around the coracoid process before the clavicle is positioned using the clavicle fixation assembly. In this way, the clavicle can be positioned by passing or sliding suture through the loop of the cerclage without requiring a surgeon to balance simultaneous installation of the cerclage and the clavicle fixation assembly.

A system configured for treatment of an acromioclavicular (AC) joint according to an exemplary aspect of the present disclosure includes, among other things, a cerclage configured to be arranged about a coracoid process. The cerclage includes a loop.

A method for treatment of an acromioclavicular (AC) joint according to an exemplary aspect of the present disclosure includes, among other things, providing a cerclage about a coracoid process such that the cerclage includes a loop, and passing a portion of a clavicle fixation assembly through the loop.

Another method according to an exemplary aspect of the present disclosure includes, among other things, providing a cerclage about a first bone such that the cerclage includes a loop, passing a strand of suture through the loop, tensioning the strand of suture, and fixing the strand of suture relative to a second bone to hold a relative position of the first and second bones.

DETAILED DESCRIPTION

Figure 1:
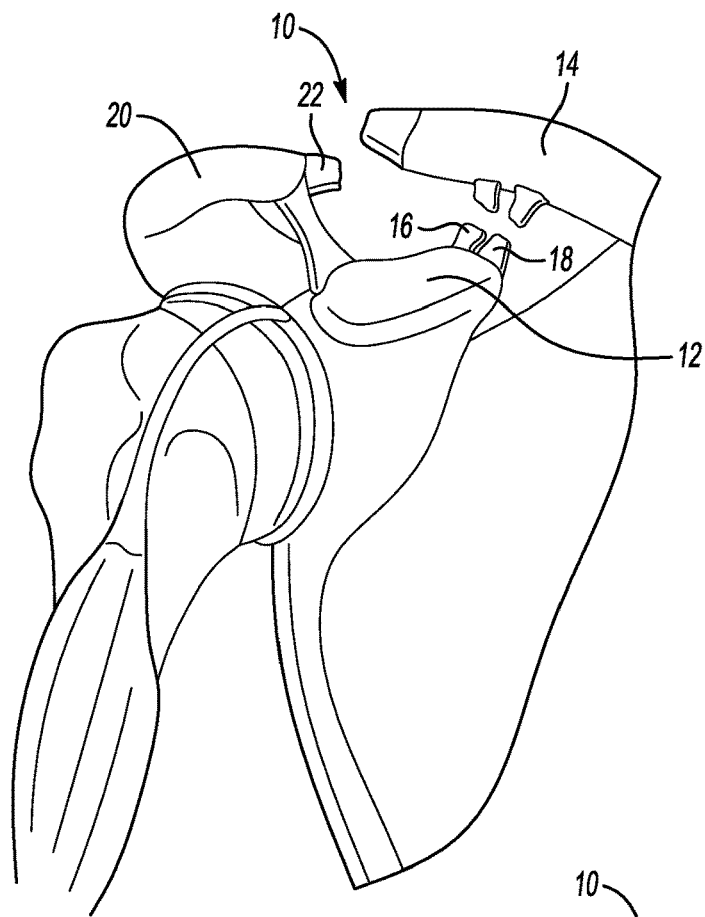
FIG. 1 illustrates a partial view of a shoulder, and in particular an acromioclavicular (AC) joint, with torn ligaments.
Figure 9:
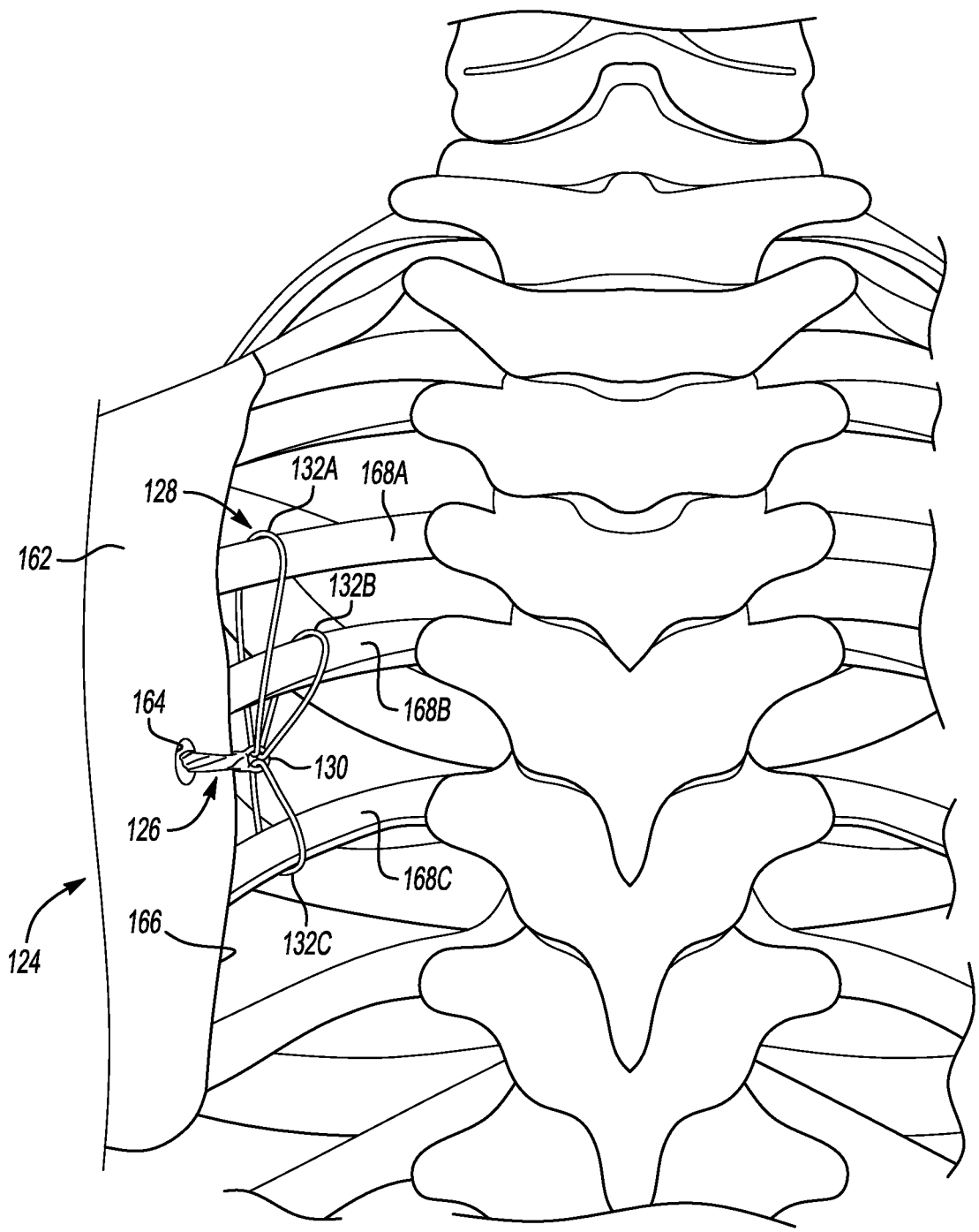
FIG. 9 illustrates a portion of a body including the thoracic spine from a posterior perspective, and in particular illustrates a system for providing a scapular fusion.
Figure 10:
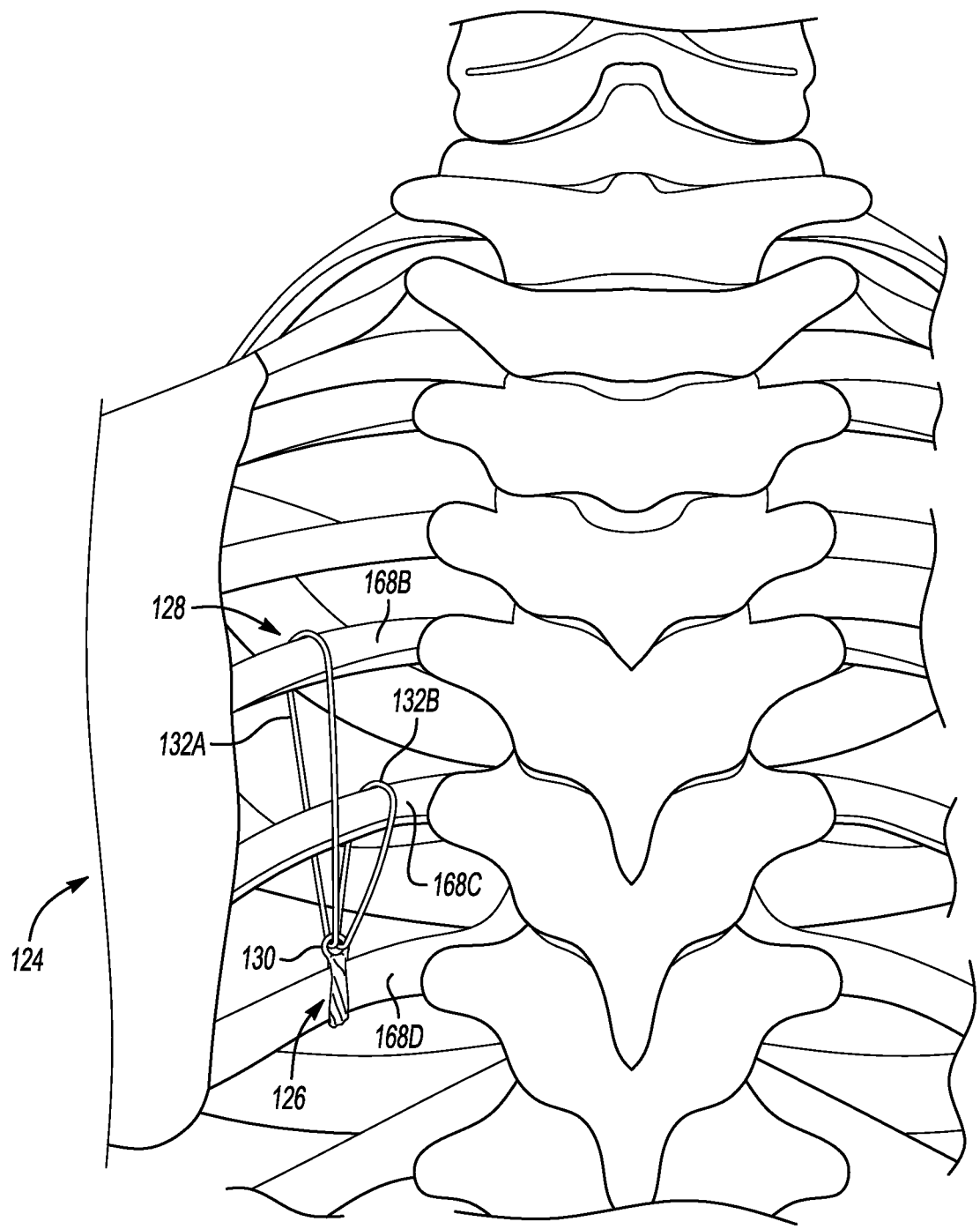
FIG. 10 illustrates the same portion of the body as FIG. 9, and in particular illustrates another system for treating a slipped or fractured rib.

This disclosure details a system and method, which is useful in treating an acromioclavicular (AC) joint. FIG. 1 is a view of an exemplary view of a shoulder, and in particular illustrates an AC joint 10 including a coracoid process 12 and a clavicle 14 superior to the coracoid process 12. In a healthy AC joint, coracoclavicular ligaments 16, 18 connect the coracoid process 12 to the clavicle 14. The AC joint 10 further includes an acromion 20 lateral to the clavicle 14 and, in a healthy AC joint 10, the acromion 20 is connected to the clavicle 14 by an acromioclavicular ligament 22. In FIG. 1, each of the ligaments 16, 18, 22 is fully torn and, as such, the clavicle 14 is out of position relative to a healthy AC joint in which those ligaments are not torn. While three fully torn ligaments are shown in FIG. 1, this disclosure is useful in treating AC joints with other defects, such as AC joints with one or more ligaments that are worn, partially torn, or fully torn. Further, this disclosure can be used outside the context of the AC joint, and in particular can be used for sternal closures, for scapular fusions (FIG. 9), or for treating fractured or dislocated ribs (FIG. 10).

Figure 2:
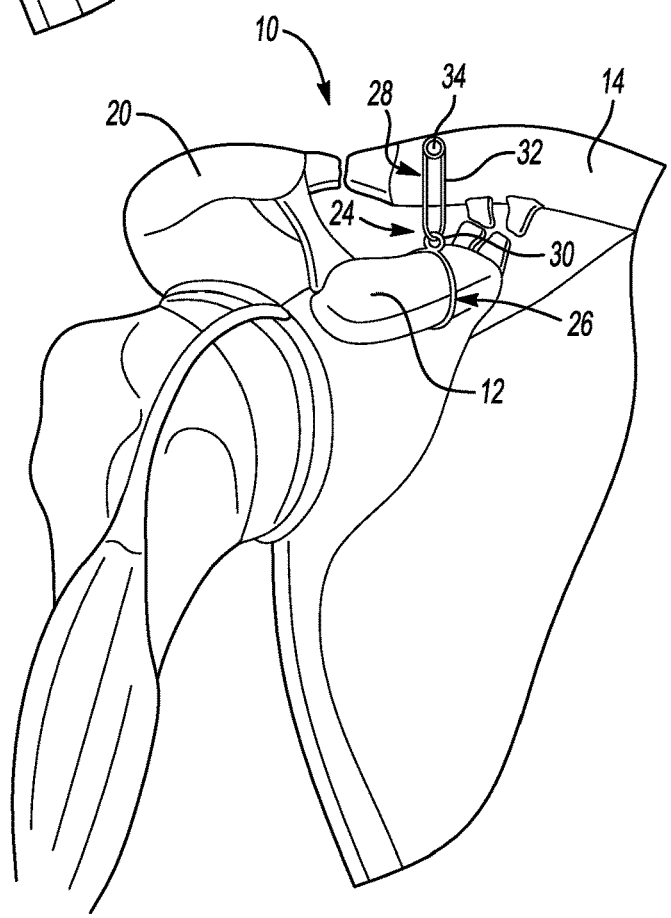
FIG. 2 illustrates a similar view of a shoulder to FIG. 1, but in FIG. 2 an example system for treating the AC joint has been installed.

FIG. 2 illustrates a system 24 configured to treat an AC joint 10. In FIG. 2, the system 24 is installed relative to the AC joint 10 and holds the clavicle 14 in a position substantially similar to that of a healthy AC joint in which the ligaments 16, 18, 22 are not torn.

The system 24 includes a cerclage 26 arranged about the coracoid process 12 and a clavicle fixation assembly 28 configured to hold the clavicle 14 in place relative to the coracoid process 12. Further, the cerclage 26 includes a loop 30, and a portion of the clavicle fixation assembly 28 is configured to pass through the loop 30. The clavicle fixation assembly 28, in this example, includes at least one strand of suture 32 passed through the loop 30 and a fixation device 34, such as an anchor like those of the PushLock® or SwiveLock® offered commercially by Arthrex, Inc., insertable into the clavicle 14 and configured to hold the suture 32 and, in turn, to hold the clavicle 14 in place. The suture 32 may be fixed relative to the clavicle 14 using a fixation device 34 other than an anchor or using another technique altogether. The suture 32 may include multiple strands of suture. The suture 32 may also include one or more strands of suture which are attached to the acromion 20. In this regard, the term clavicle fixation assembly 28 is inclusive of sutures connected to other bones, such as the acromion.

Figure 3:
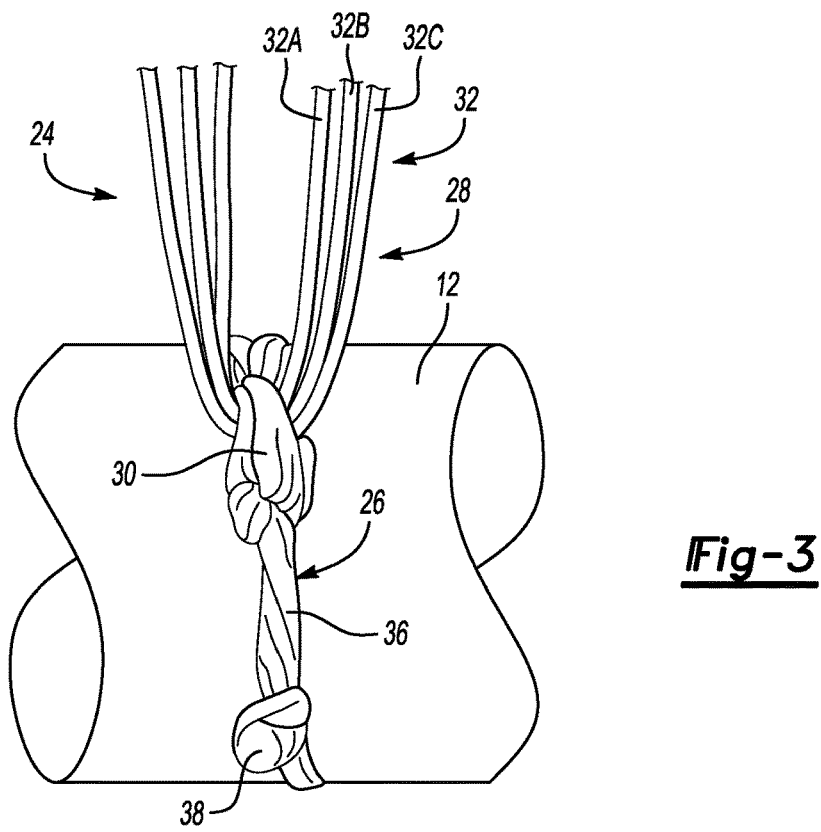
FIG. 3 is a partial, close-up view of the system for treating the AC joint of FIG. 2.

FIG. 3 is a partial, close-up view of the system 24 arranged relative to the coracoid process 12. As shown, the cerclage 26 is arranged about the coracoid process 12. The cerclage 26 is tightened firmly against, and directly contacts, an outer surface of the coracoid process 12. The cerclage 26 extends about the entirety of the coracoid process 12. The cerclage 26, in this example, is made of a strand of suture 36.

In an example, the suture 36 forming the cerclage 26 is a high strength braided suture, such as Arthrex, Inc.'s Fiber-Tape®. The suture 36 may include a multifilament cover formed of a plurality of braided fibers of ultrahigh molecular weight polyethylene (UHMWPE) and fibers of polyester. The cover may surround a core formed of twisted fibers of ultrahigh molecular weight polyethylene (UHMWPE). Other types of suture come within the scope of this disclosure, however.

In FIG. 3, the suture 32 of the clavicle fixation assembly 28 includes three strands of suture 32A-32C, each passing through the loop 30. The strands of suture 32A-32C may be made of the same type of suture as the cerclage 26 or another type of suture. Each of the three strands of suture 32A-32C is tensioned and fixed to either the cerclage 14 or the acromion 20 using a fixation device such as the fixation device 34.

In the example of FIG. 3, the loop 30, which is a shape produced by a curve that bends around an crosses itself, is formed by tying the suture 36 in at least one knot. In this way, the cerclage 26 and loop 30 are both formed of the suture 36, and the loop 30 is integrally formed with the cerclage 26. The loop 30 could be provided by a separate structure, however, which may be attached to the cerclage 26 by being sewn into the cerclage or by using some other attachment technique. In an example, a rigid eyelet made of a high strength, rigid polymer is sewn into the suture 36 to provide the cerclage 26 with the loop 30. In another example, a through-hole may be formed in the suture 36, such as by punching, and the through-hole may provide the loop 30. An eyelet or stitching may provide a boundary of the through-hole.

After arranging the cerclage 26 about the coracoid process 12, the cerclage 26 is tightened, the loop 30 is arranged near a superior portion of the coracoid process 12, and a knot 38 is tied to hold the cerclage 26 in place. The knot 38 may include one or more known types of knots, including surgical knots. The strands of suture 32A-32C can pass freely through the loop 30 to position the clavicle 14 and/or acromion 20.

While the term cerclage is often used to refer to rings or loops of material that bind together fractured bones, the cerclage 26 is arranged relative to a healthy coracoid process 12, in this example. The cerclage 26 itself is a ring or loop arranged about the coracoid process 12, which includes an additional loop 30, which in turn is used to maintain a position of the clavicle 14 and/or the acromion 20 to treat and/or stabilize the same. Use of the term cerclage in this disclosure does not denote that the bone being cerclaged is fractured.

An example method of providing the cerclage 26 relative to the coracoid process 12, including forming the loop 30, will now be described. A surgeon may perform the method either partially or entirely. One or more steps of the method may be performed by a manufacturer or surgical assistant. The method may be performed either partially or entirely during an arthroscopic surgical procedure.

Figure 4:
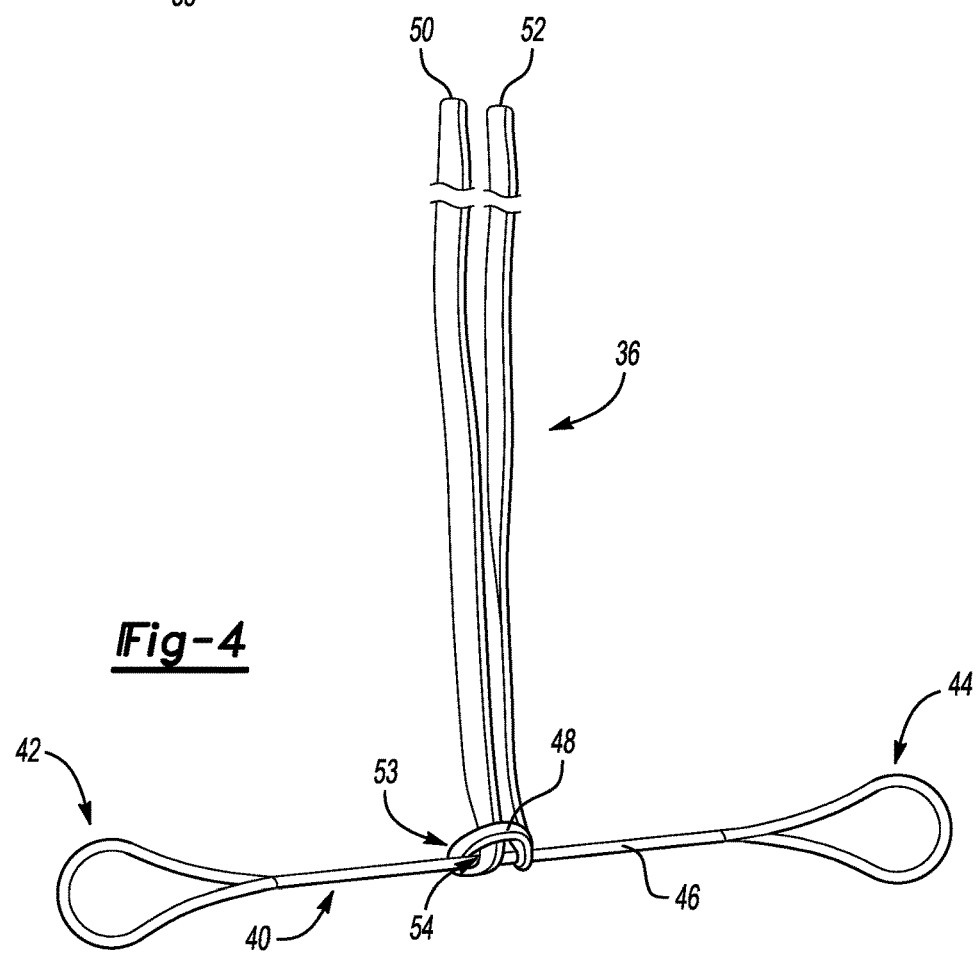
FIG. 4 illustrates a step of an example method, and in particular illustrates a suture tied relative to a pull-through suture using a hitch knot.

With reference to FIG. 4, the suture 36 used for the cerclage 26 is provided and is arranged relative to a pull-through suture 40. The pull-through suture 40 includes a first end loop 42 and a second end loop 44 opposite the first end loop. A main section 46 connects the first and second end loops 42, 44. The pull-through suture 40 may be provided by a strand of suture, such as a monofilament suture, and in one example is a thinner suture than the suture 36. The first and second end loops 42, 44 may be provided by splicing and/or stitching relative to the main section 46. The use of the pull-through 40 suture will be described below. The pull-through suture 40 does not form part of the as-installed cerclage 26 and instead is only used during the process of installing the cerclage 26.

In FIG. 4, the suture 36 is folded such that it exhibits a folded end 48 and first and second free ends 50, 52. The suture 36 is tied into a cow hitch knot 53 about the main section 46 of the pull-through suture 40, in this example. While a cow hitch knot is mentioned, other types of knots, such as other types of hitch knots, may be used, however. The cow hitch knot 53 is arranged such that the suture 36 exhibits a pull-through loop 54 adjacent the main section 46. Tying the cow hitch knot 53 relative to the pull-through suture 40 may be referred to as preloading the pull-through suture 40 into the pull-through loop 54, since this step may be done pre-operatively or before wrapping the suture 36 around the coracoid process 12.

Figure 5:
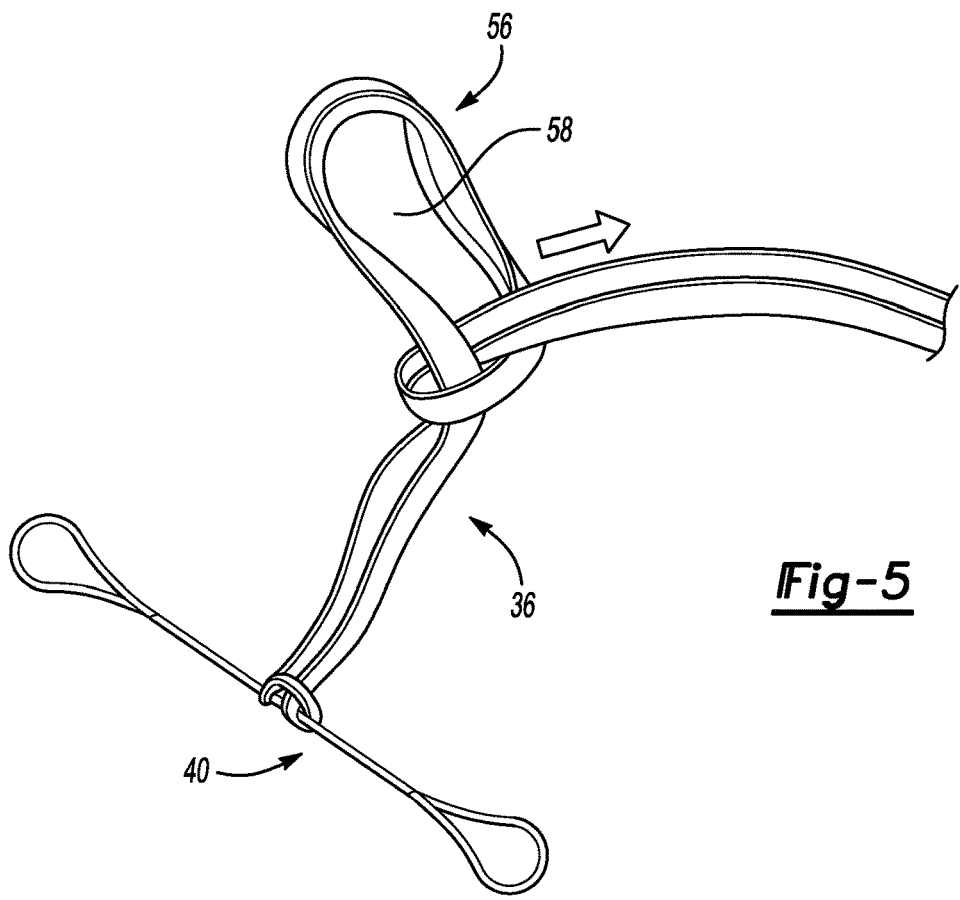
FIG. 5 illustrates a step of the example method, and in particular illustrates the suture being tied into a first overhand knot.

Next, the suture 36 is tied to provide the loop 30. As shown, the suture 36 exhibits two lengths between the folded end 48 and the first and second free ends 50, 52. As represented in FIG. 5, the lengths are held together and simultaneously tied, as one, into a first overhand knot 56. Another type of knot may be used. The first overhand knot 56 is held loose such that it exhibits an opening 58 provided by two lengths of the suture 36, which will ultimately form the opening of the loop 30. The loop 30, in this regard, is provided by two looped lengths of suture 36, which provides a robust connection point for the clavicle fixation assembly 28.

Figure 6:
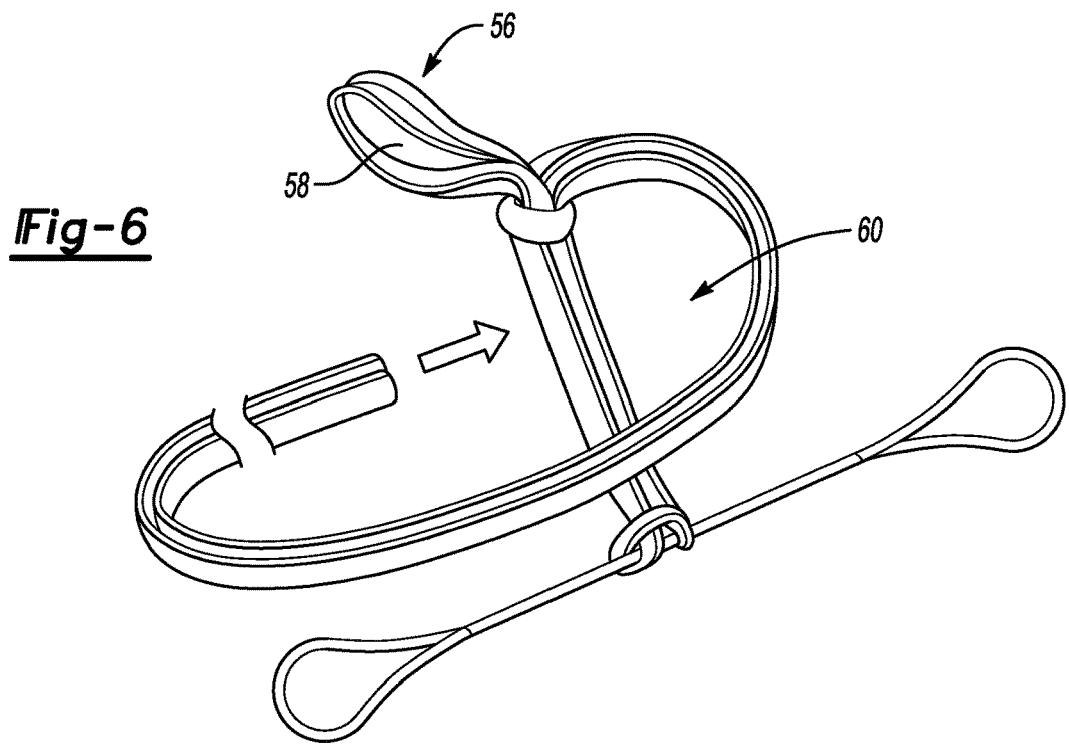
FIG. 6 illustrates a step of the example method, and in particular illustrates the suture being tied into a second overhand knot.

Next, as represented in FIG. 6, another knot is tied adjacent the first overhand knot 56. In FIG. 6, a second overhand knot 60 is tied. The second overhand knot 60 is fully tightened adjacent the first overhand knot 56 to hold the opening 58 in place, such that the opening 58, and in turn the loop 30, is prevented from closing. Thus, additional suture, such as that of the clavicle fixation assembly 28, can pass through the loop 30.

As mentioned, one or more steps of the method may be performed before a surgical procedure. In a particular example, the steps represented by FIGS. 4-6 may be performed pre-operatively by a surgical assistant or a manufacturer.

Figure 7:
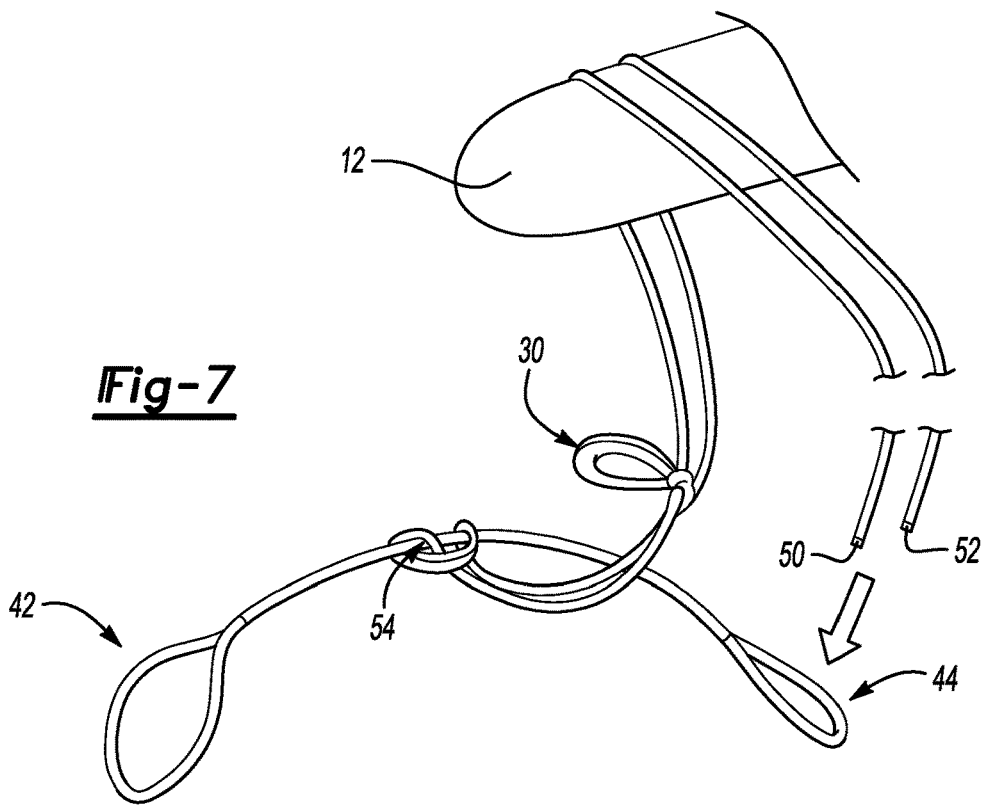
FIG. 7 illustrates a step of the example method, and in particular illustrates free ends of the suture being inserted into a loop of the pull-through suture.
Figure 8:
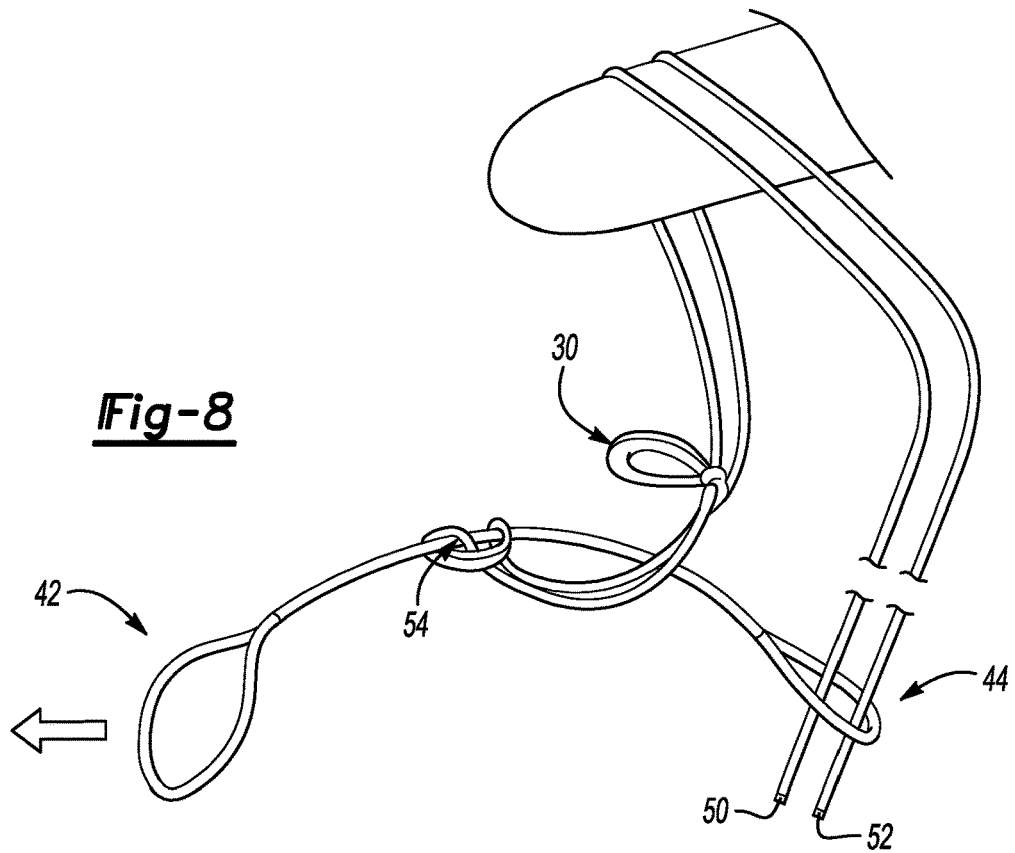
FIG. 8 illustrates a step of the example method, and in particular illustrates a force being applied to another loop of the pull-through suture such that the free ends are pulled through the hitch knot.

Once the construct of FIGS. 4-6 is formed, the first and second free ends 50, 52 are passed around the coracoid process 12 during a surgical procedure, as generally shown in FIG. 7. The first and second free ends 50, 52 are then inserted into one of the first or second end loops 42, 44. In FIG. 7, first and second free ends 50, 52 are both inserted into the second end loop 44. Then, as represented in FIG. 8, the surgeon applies a force to the first end loop 42 to pull the second end loop 44, and in turn the first and second free ends 50, 52, through the pull-through loop 54. The first and second free ends 50, 52 are then further pulled in the same direction to tighten the cerclage 26 about the coracoid process 12. The knot 38 is then tied and trimmed, if necessary.

With the cerclage 26 in place, the clavicle fixation assembly 28 may then be installed, such as by passing the suture 32 through the loop 30, tensioning the suture 32 to provide a desired position of the clavicle 14 and/or acromion, and fixing the at least one suture 32 in place relative to the clavicle 14 and/or acromion 20. While an example method has been described, this disclosure extends to variations of the above-described method.

As mentioned above, this disclosure can be used outside the context of the AC joint. FIGS. 9 and 10 illustrate two such examples. FIGS. 9 and 10 illustrate a system 124 similar to the system 24 with like parts preappended with a "1." The system 124 is used relative to bones adjacent the thoracic spine.

With reference to FIG. 9, a cerclage 126 is provided relative to a scapula 162. The cerclage 126 is provided through a hole 164, which may be drilled, in the scapula 162 and is wrapped about a medial edge 166 of the scapula 162. The cerclage 126 is arranged such that the loop 130 projects medially of the medial edge 166. The cerclage 126 is formed and placed using a technique similar to that described above and shown relative to FIGS. 4-8. A fixation assembly 128 including a plurality of strands of suture 132A, 132B, 132C is used to apply tension to the scapula 162 and to hold the scapula 162 relative to ribs 168A, 168B, 168C, thereby providing a scapula fusion.

In another example, the system 124 may be used to treat a slipped or fractured rib. With reference to FIG. 10, the system 124 includes a cerclage 126 provided about a rib 168D which is either slipped or fractured. The cerclage 126 is formed and placed using a technique similar to that described above and shown relative to FIGS. 4-8, and the cerclage 126 is arranged about the rib 168D such that the loop 130 projects from the rib 168D in a direction, here a superior direction, toward other, healthy ribs 168B, 168C to which the fixation assembly 128 will attach. In this example, the fixation assembly 128 includes two stands of suture 132A, 132B passed through the loop 130 and attached to a respective one of the ribs 168B, 168C. Before being attached to the ribs 168B, 168C, the strands of suture 132A, 132B are tensioned to position the rib 168D in a desired position to promote healing.

It should be understood that directional terms such as superior, medial, and lateral are used herein consistent with their art-accepted meaning. These terms should not otherwise be considered limiting.

Although the different examples have the specific components shown in the illustrations, embodiments of this disclosure are not limited to those particular combinations. It is possible to use some of the components or features from one of the examples in combination with features or components from another one of the examples. In addition, the various FIGS. accompanying this disclosure are not necessarily to scale, and some features may be exaggerated or minimized to show certain details of a particular component or arrangement.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A method for treatment of an acromioclavicular (AC) joint, comprising:
    providing a cerclage about a coracoid process such that the cerclage includes a loop, wherein the cerclage is provided by folding a first strand of suture to provide the first strand of suture with a folded end and first and second free ends, and wherein the loop is provided by tying the first strand of suture adjacent the folded end; and
    passing a portion of a clavicle fixation assembly through the loop.

2. The method as recited in claim 1, further comprising:
    tying the first strand of suture to provide a pull-through loop adjacent the folded end; and
    pulling the first and second free ends through the pull-through loop to tighten the cerclage against an outer surface of the coracoid process.

3. The method as recited in claim 1, further comprising:
    attaching a portion of the clavicle fixation assembly to a clavicle.

4. The method as recited in claim 3, wherein the portion of the clavicle fixation assembly includes a second strand of suture, and further comprising a step of positioning the clavicle relative to the coracoid process by applying force to the second strand of suture.

5. A method, comprising:
    providing a cerclage about a first bone such that the cerclage includes a loop, wherein the cerclage is provided by folding a first strand of suture to provide the first strand of suture with a folded end and first and second free ends, and wherein the loop is provided by tying the first strand of suture adjacent the folded end;
    after the cerclage is formed, passing a second strand of suture through the loop;
    tensioning the second strand of suture; and
    fixing the second strand of suture relative to a second bone to hold a relative position of the first and second bones.

* * * * *